United States Patent [19]

Roginski

[11] Patent Number: 4,927,545

[45] Date of Patent: May 22, 1990

[54] METHOD AND APPARATUS FOR AUTOMATIC PROCESSING AND ANALYZING OF BLOOD SERUM

[75] Inventor: Edward T. Roginski, Hamtramck, Mich.

[73] Assignee: Medical Automation Specialties, Inc., Detroit, Mich.

[21] Appl. No.: 254,420

[22] Filed: Oct. 6, 1988

[51] Int. Cl.$^5$ ............................................. B01D 21/26
[52] U.S. Cl. ..................................... 210/745; 210/85; 210/91; 210/94; 210/104; 210/142; 210/360.1; 210/416.1; 210/518; 210/782; 210/789; 422/67; 422/72; 422/106; 436/45; 436/48; 494/10; 494/37; 73/61.4
[58] Field of Search ................ 210/745, 782, 789, 787, 210/85, 91, 94, 104, 142, 360.1, 406, 416.1, 515, 516, 518; 494/10, 16, 37; 422/65, 67, 72, 106, 108; 436/45, 48, 55, 177, 180; 356/39; 73/61.4; 346/33 ME

[56] References Cited

U.S. PATENT DOCUMENTS

| | | | |
|---|---|---|---|
| 3,882,716 | 5/1975 | Beiman | 210/325 |
| 4,118,974 | 10/1978 | Nozaki et al. | 73/61.4 |
| 4,120,662 | 10/1978 | Fosslien | 422/100 |
| 4,311,484 | 1/1982 | Fosslien | 422/65 |
| 4,326,851 | 4/1982 | Bello et al. | 204/1 T |
| 4,464,167 | 8/1984 | Schoendorfer | 494/37 |
| 4,478,095 | 10/1984 | Bradley et al. | 422/67 |
| 4,713,974 | 12/1987 | Stone | 422/67 |
| 4,828,716 | 5/1989 | McEwen et al. | 210/745 |

FOREIGN PATENT DOCUMENTS 2825659  12/1979  Fed. Rep. of Germany ........ 356/39

Primary Examiner—W. Gary Jones
Attorney, Agent, or Firm—Krass & Young

[57] ABSTRACT

An apparatus for processing and analyzing blood serum includes an input rack for holding test tubes containing whole blood specimens and separator gel, a centrifuge, an optical sensing unit for receiving centrifuged test tubes and generating output signals indicative of whether the centrifuging was successful and, if it was, the boundary position between the separator gel and the blood serum, and a computer connected to receive and analyze the output signals of the optical sensing unit. An aspirator/dispenser needle unit is positioned above the sensing unit and is capable of lowering a needle, under the control of the computer, to puncture the stopper of a test tube and then withdraw blood serum. The apparatus also includes a cup feeder station for storing and dispensing empty cups for receiving and holding blood serum dispensed from the needle, an noutput rack for holding cups containing blood serum samples along with the corresponding test tubes, a bar code reader for identifying test tubes, and a disposal station for receiving test tubes determined to be defective by the computer. A robotic arm moves the tube from station to station under the control of the computer.

17 Claims, 3 Drawing Sheets

METHOD AND APPARATUS FOR AUTOMATIC PROCESSING AND ANALYZING OF BLOOD SERUM

BACKGROUND OF THE INVENTION

A. Field of the Invention

This invention relates to apparatus and a method for processing and analyzing blood serum and more particularly to a system that automatically processes whole blood specimens to separate and withdraw the blood serum from the red blood cells and that also removes from further processing those specimens which are defective before the blood serum is withdrawn.

B. Description of Related Art

The process of separating the red blood cells from the blood serum of a whole blood specimen by centrifuge and then removing the blood serum is conducted on a large scale in hospitals and laboratories. This process is usually conducted manually by a technician. In the process, a stopper sealed test tube, containing a whole blood specimen and a separating gel, is centrifuged so that its contents are separated into three layers, a top layer containing the serum, a middle layer containing the separating gel, and a bottom layer containing the red blood cells. After the test tube is centrifuged, the technician must examine the blood specimen to determine whether it is defective. If the sample is not defective, the technician then inserts a needle through the rubber stopper, eyes the placement of the needle in order to insure the needle does not contact the separating gel, and withdraws a sample of the blood serum from the top layer and places the sample into a cup. Efficiency, accuracy, and maintaining the integrity of the blood specimen are essential to this process. More important is the safety of the technician while completing the process. By fully automating this process, these factors are greatly enhanced. The danger to the technician of being exposed to any transmitted diseases in the specimens during this process is eliminated.

U.S. Pat. Nos. 4,713,974 and 4,478,095 disclose devices for automatically piercing container lids and withdrawing samples. Neither of these patents disclose any means for sensing an appropriate level inside the test tube for positioning the tip of the sampling needle. Also, these patents do not disclose devices for use with centrifuged blood samples and do not disclose any means for automatically detecting defective samples.

U.S. Pat. Nos. 4,120,662 and 4,311,484 both disclose blood sample processing systems for delivering blood from closed vacutainers to a Coulter Counter. These systems are not suitable for use with centrifuged blood samples in that tubes are sampled in an approximately horizontal position and are agitated prior to sampling.

U.S. Pat. No. 4,326,851 discloses a level sensor for use with a fluid transfer mechanism for determining when the bottom tip of a fluid aspirating probe touches the top surface of a sample fluid. This device cannot be used with blood samples in conventional test tubes. In addition, the patent discloses no method or apparatus for automatically sensing whether the sample is defective.

SUMMARY OF THE INVENTION

This invention is accordingly directed toward apparatus and a method for automatically centrifuging blood specimens and separating gels in stopper sealed test tubes, determining whether the centrifuged specimens are defective, and removing and then dispensing blood serum samples from only those sealed test tubes in which the specimens are not defective.

The method of the present invention includes centrifuging a test tube containing a whole blood specimen and separator wax, moving the test tube into an optical sensing unit, and analyzing the electrical signals generated by the sensing unit to evaluate the success of the separation and to determine the position of the boundary surface between the separator wax and the blood serum.

In the preferred embodiment, the optical sensing unit includes a vertical cavity operative to receive a test tube. The cavity includes a light source disposed on one of its sides that emits a light beam that extends generally normally to the longitudinal axis of a test tube placed in the cavity. The cavity also includes at least one photosensor disposed on its opposite side and positioned to receive the transmitted portion of the light beam. The photosensor generates electrical signals proportional to the amplitude of the transmitted beam. The apparatus of the present invention further includes means for receiving these electrical signals and analyzing them to evaluate the success of the separation, and to determine the position of the boundary surface between the separator wax and the blood serum along the longitudinal axis of the tube.

In an alternative embodiment, the vertical cavity of the optical sensing unit includes a vertical array of photosensors disposed on one side of the cavity and a corresponding vertical array of light sources disposed on the opposite side of the cavity. Each of the plurality of light beams emitted from the light sources extend generally normally to the longitudinal axis of a test tube placed in the cavity. The photosensors each receive the light beams transmitted from their corresponding light sources and generate electrical signals proportional to the amplitude of the transmitted beams.

The apparatus of the present invention also includes an input station adapted to hold test tubes each containing whole blood specimens and separator wax, and a centrifuge for separating the whole blood into serum and red cells separated by a layer of separator wax.

The apparatus further includes a needle apparatus, responsive to the means for determining the position of the boundary surface between the separator wax and the blood serum, connected to suction means for insertion into a test tube and for drawing a blood serum sample from the tube. The needle apparatus is also connected to means for dispensing the serum that was drawn out of test tubes by the suction means.

The apparatus also includes a pair of output stations for receiving both successfully and unsuccessfully separated test tubes, and a robotic arm for moving the test tubes from station to station, under the control of the means for evaluating the electrical signals generated by the photosenor(s).

The preferred embodiment also includes a feeder station adapted to dispense empty containers that are operative to hold blood serum samples. The robotic arm is also adapted, under the control of the means for evaluating the electrical signals generated by the photosensor(s), to remove an empty container from the feeder station and to move it to a position underneath the needle apparatus.

The present invention makes the process of centrifuging and analyzing blood specimens efficient and accurate. It also eliminates the danger of a technician being exposed to any transmitted disease, such as AIDS, during the process.

BRIEF DESCRIPTION OF THE DRAWINGS

Other objectives, advantages, and applications of the present invention will be made apparent by the following detailed description of the preferred embodiment of the invention. The description makes reference to the accompanying drawings in which.

DETAILED DESCRIPTION OF THE PREFERRED EMBODIMENT

Figures 1, 2:
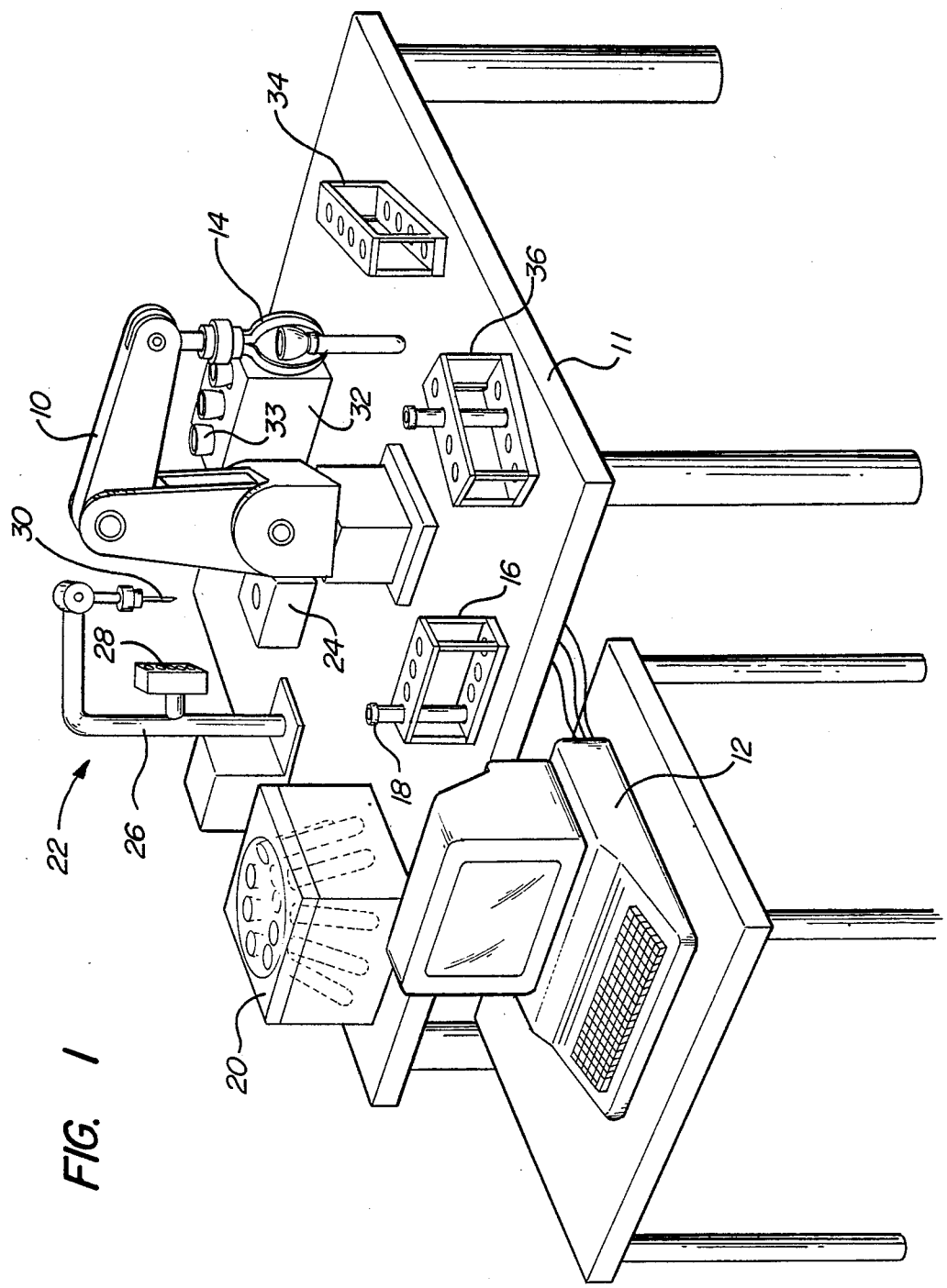
FIG. 1 is a perspective view of the preferred embodiment of the automatic blood serum processor and analyzer.
FIG. 2 is a cross-sectional view of a test tube, containing a centrifuged blood specimen, of the type used in the present invention.

Referring to FIG. 1, the preferred embodiment of the present invention is supported on a work station 11. In FIG. 1, a robotic arm, generally indicated at 10, is positioned so that it can axially rotate about a vertical axis to reach any of six different stations. The robotic arm is connected to a control computer 12. In the preferred embodiment, the robot is a five axis articulated arm. Such robotic arms are well known to the art. The robotic arm 10 includes a multi-purpose gripper 14 of conventional construction.

The first station constitutes a rack 16 for holding test tubes 18 of conventional construction. The rack may be either manually loaded by an operator, or automatically loaded. In the preferred embodiment each test tube is bar coded for identification purposes. The bar code is read either by the robot 10 or by equipment at the hospital or clinic where the blood was drawn. The second station is a centrifuge 20. The centrifuge is used to centrifuge whole blood specimens along with separating gels in stopper sealed test tubes by rotating the tubes inclined with respect to a vertical axis about that axis so that the contents of the test tubes are separated, as indicated in FIG. 2, into a top layer 40 containing the blood serum, a middle layer 42 containing the separating gel, and a bottom layer 44 containing the red blood cells. The separator gel (or wax) has a density half-way between the densities of the serum and the red blood cells. As indicated in FIG. 2, after centrifuging the separator gel may not lie in a horizontal plane normal to the longitudinal axis of the test tube, but rather at an angle from the horizontal plane. The orientation of the middle layer 42 is determined by the type of centrifuge used. Centrifuges are well known to the art.

The third station is a serum sensing and aspirator/dispenser unit, generally indicated at 22. This station includes an optical blood serum sensing unit 24, and an aspirator/dispenser unit 26. The station 22 also includes a bar code reader 28 of conventional construction. Both the sensor and the aspirator/dispenser units are connected to the control computer 12. The optical sensor 24 receives test tubes containing centrifuged blood specimens and outputs signals to the computer 12 so that the computer may determine whether the specimen is defective, and, if it is not, an appropriate level in the test tube to position the tip of an aspirator needle for removing a blood serum sample. The aspirator/dispenser unit 26 functions, under the control of computer 12, to lower a sampling needle 30 to puncture the stopper seal of a test tube held in the optical sensor 24, for withdrawing samples from the test tube. Automatic aspirator/dispensers are well known to the art.

The fourth station is a serum cup feeder 32 that stores empty cups 33 for holding blood serum samples dispensed by the aspirator/dispenser unit 26. The serum sample cup is preferably formed of plastic. The fifth station is an output rack 34 for holding cups containing blood serum samples along with their corresponding test tubes. Finally, the sixth station is a rejection unit 36 for receiving those test tubes which are determined defective by the computer 12.

The preferred embodiment of the present invention operates, under the control of computer 12, as follows:

First, the robotic arm 10 loads test tubes, each containing whole blood specimens and separating gel, into the centrifuge 20 one by one from the input rack 16. The centrifuge 20 is then activated. After the centrifuging process is completed, the robotic arm 10 removes the centrifuged test tubes, one by one, from the centrifuge 20 and places them into the optical sensor 24.

If the signals from the optical sensor 24 indicate that the centrifuging results in lipemic (white), hymolized (red) or otherwise unsuccessful specimen, then the robotic arm 10 removes the test tube from the sensor 24 and places it in the rejection unit 36.

If the signals from the optical sensor 24 indicate the specimen is not defective, the sampling needle 30 of the aspirator/dispenser unit 26 is lowered to puncture the stopper seal of the test tube and to the level in the test tube previously determined by the analysis of the output signals from the optical sensor 24. A sample of the blood serum is drawn from the test tube through the needle 30 by the aspirator unit. In the preferred embodiment of the invention, approximately 1.5 milliliters of blood serum is withdrawn.

At the same time that the blood serum is being withdrawn, the robotic arm 10 removes an empty serum cup from the serum cup feeder 32, using the gripper 14. After the blood serum sample is withdrawn from the test tube, the aspirator/dispenser unit 26 lifts the sampling needle 30 out of the test tube into a stow position. The robotic arm 10 then moves the empty serum cup into a position underneath the sampling needle 30. The aspirator/dispenser unit 26 then dispenses the blood serum sample through the sampling needle 30 and into the cup that is supported by the robotic arm 10.

After the cup receives the blood serum sample, the robotic arm places the cup on top of the stopper seal of the test tube resting in the optical sensor 24. The robotic arm 10 then removes the test tube, along with the serum sample cup, from the optical sensor 24, positions it by the bar code reader 28 for identification purposes, and places the test tube along with the serum sample cup in the output rack 34. In the preferred embodiment of the invention, the serum sample cup is constructed so as to snugly fit on top of a stopper.

The above process is repeated until all centrifuged test tubes are examined. The system may then load a new batch of test tubes into the centrifuge.

Figure 3:
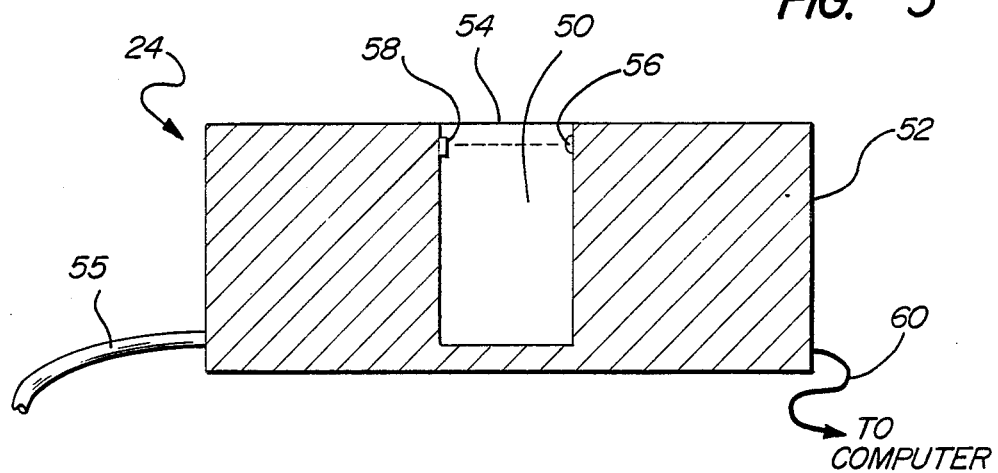
FIG. 3 is a cross-sectional view of the optical sensor of the preferred embodiment of the present invention.

FIG. 3 is a cross-sectional view of the optical sensor 24 of the preferred embodiment of the present invention. The sensor 24 is located in a vertical cavity, generally indicated at 50, of a housing 52. The vertical cavity 50 has an opening 54, and is adapted to receive a test tube of conventional construction. The sensor 24 is connected to a power source via a power cord 55.

A light source 56 is disposed on one side of the cavity 50, near the opening 54. The beam emitted by the light source 56 extends generally normally to the longitudinal axis of a test tube placed in the cavity 50. In the preferred embodiment, the light beam is a pulsed infrared rectangular sliver of light extending across the diameter of the cavity 50. The beam is pulsed at a high frequency to avoid ambient noise.

A sensor 58 is disposed on the opposite side of cavity 50 from the light source 56 so as to receive the transmitted portion of the light beam emitted from the light source. In the preferred embodiment, the sensor is a horizontal array of photosensors adapted to receive the entire sliver of light when the cavity is empty. Optical filters that only transmit light having the frequency of light source 56 are positioned in front of the photosensors in order to avoid noise. The contents of a test tube displaced between the light source 56 and the sensor 58 will partially occlude the light beam from the sensors. The sensors have an analog output proportional to the portion of the beam that is occluded. The sensor 58 is connected to the control computer 12 via a connection line 60 in order to provide it with the outputs of the photosensors. In the preferred embodiment, the output from photosensors is passed through an analog to digital converter before being received by the computer 12.

The control computer 12 processes the signals received from the optical sensor 24 in order to determine the success of the centrifuge separation and the level of the separator wax (the middle layer) in the centrifuged specimen. In the preferred embodiment of the present invention, the robotic arm 10 is controlled to lower the centrifuged test tube to be analyzed down through the opening 54 and into the cavity 50 of the optical sensor 24. While the robotic arm 10 is moving the tube down into the cavity 50, the computer 12 receives the output signals from the sensor 58. If a successfully centrifuged blood specimen, as indicated in FIG. 2, is being moved into the cavity 50, first the light beam is occluded to a relatively high degree by the bottom layer 44 of red blood cells, then to a lesser degree by the middle layer 42 of separator wax, and then to an even lesser degree by the top layer 40 of blood serum.

If the output signals from the optical sensor 24 do not indicate these three layers, then the robotic arm removes the test tube from the optical sensor and places it in the rejection unit 36. In the case where the centrifuging is successful, knowledge of the position of the test tube relative the optical sensor at the point in which the sensor 58 signals indicate a transition between the separator wax and the blood serum allows the computer 12 to determine a level, spaced above the separator wax, for positioning the sampling needle 30 of the aspirator/dispenser unit 26.

Figure 6:
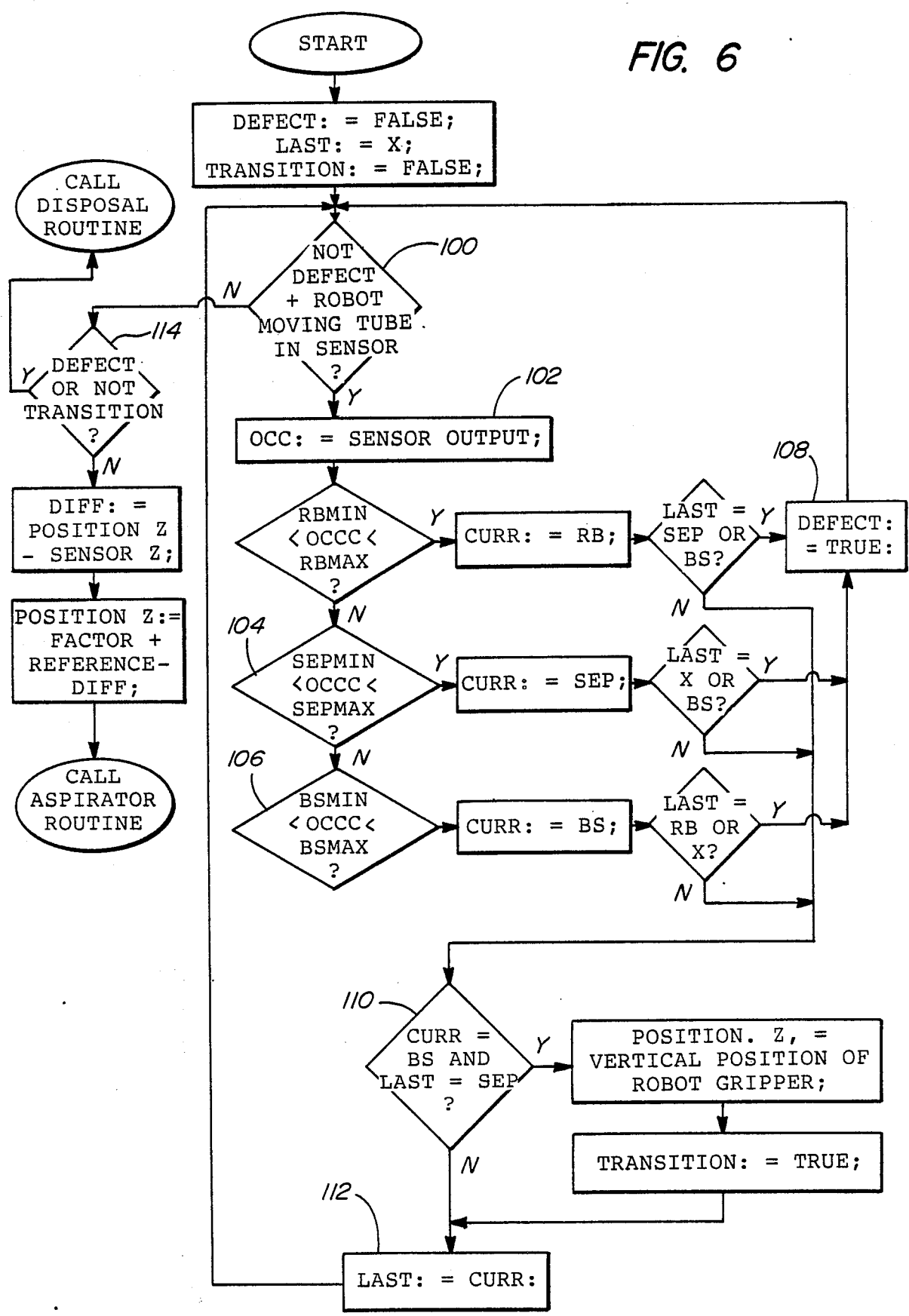
FIG. 6 is a general flow diagram of the algorithm for evaluating the output of the optical sensor of the preferred embodiment of the present invention.

FIG. 6 is a general flow diagram for the algorithm used by the computer 12 in evaluating the outputs from the optical sensor 24 in the preferred embodiment of the invention. For the purposes of illustration, well-known housekeeping functions, such as error checking features, have been omitted from the flow diagram of FIG. 6.

The algorithm makes use of the following variables:

DEFECT: boolean variable for indicating whether the specimen is defective;

LAST: indicates the which portion of the centrifuged blood sample was last in between the sensor and the light source—X (for initialization), RB (for red blood cells), SEP (for separation wax), and BS (for blood serum);

TRANSITION: boolean, set to true when sensor first detects blood serum;

OCCL: variable for reading in amount of occlusion sensed by sensor 58;

RBMIN, RBMAX: constants representing the minimum and maximum values of OCCL that would indicate red blood cells;

SEPMIN, SEPMAX: constants representing the minimum and maximum values of OCCL that would indicate for separator wax;

BSMIN, BSMAX: constants representing the minimum and maximum values of OCCL that would indicate for blood serum;

CURR: same type as LAST, for storing the current portion of the centrifuged blood serum between the sensor and the light source;

POSITION.Z: for storing the vertical position of the robot gripper;

FACTOR: a constant;

REFERENCE: vertical position of robot gripper when holding a test tube that is fully placed in the optical sensor; and SENSOR.Z: vertical position of the sensor 58.

First, the algorithm initializes DEFECT to false, LAST to X, and TRANSITION to false. Next, at the step indicated at 100, it is checked whether DEFECT is false, the robot arm is moving the tube into the sensor, and TRANSITION is false. If one of the above conditions is not true, then the algorithm goes to the step indicated at 114. Otherwise, the algorithm continues at step 102.

At 102, the output from sensor 58 is read into the variable OCCL. Then, it is checked whether the value of OCCL is in the range that indicates the sensors are detecting red blood cells. If it is not, the algorithm goes to the step indicated at 104. If the sensor is detecting red blood cells, CURR is set to RB and it is checked whether the last sensor read indicated separator wax or blood serum. If not, the algorithm skips to the step indicated at 110. If the variable LAST is set to either SEP or BS, then the algorithm goes to the step indicated at 108.

At 104, it is checked whether the variable OCCL is set to a value indicative of separator wax. If not, the algorithm continues at the step indicated at 106. If so, CURR is set to SEP, and it is checked whether LAST is set to X (just initialized) or BS (the last sensor read indicated blood serum). If LAST is not set to either of these values, the algorithm continues at the step indicated at 110. If LAST is set to either X or BS, the algorithm goes to step 108.

At 106, it is checked whether OCCL is set to a value indicative of the sensors detecting blood serum. If not, the algorithm skips to step 108. If so, CURR is set to BS, and it is checked whether LAST is set to either RB or X. If not, the algorithm skips to step 110. If, however, LAST is set to either RB or X, the algorithm skips to step 108.

At step 108, DEFECT is set to true. Next, the algorithm continues at the step indicated at 100.

At step 110, it is checked whether both CURR is set to BS and LAST is set to SEP. If not, the algorithm continues at the step indicated at 112. If so, POSITION.Z is set to the vertical position of the robot gripper and TRANSITION is set to true. The algorithm then continues at step 112.

At 112, LAST is set to CURR, and the algorithm jumps back to step 100.

At 114, it is checked whether either DEFECT is true, or transition is false. If so, the centrifuged blood specimen is defective and a routine for controlling the robotic arm to dispose of the defective test tube is called. If both DEFECT is false and TRANSITION is true, then POSITION.Z is set to FACTOR +REFERENCE−(POSITION.Z−SENSOR.Z). This is the desired vertical position for positioning a sampling needle in the test tube for withdrawing blood serum. Next, a routine is called to control the aspirator/dispenser unit to withdraw the blood serum.

The description of the above algorithm is not intended to limit the present invention. Many different algorithms may be implemented for the purposes of the invention. In alternative embodiments, the sensor and analyzing algorithm may be further adapted to sense discolorizations in the specimen that would indicate an unsuccessful centrifuging.

Figure 5:
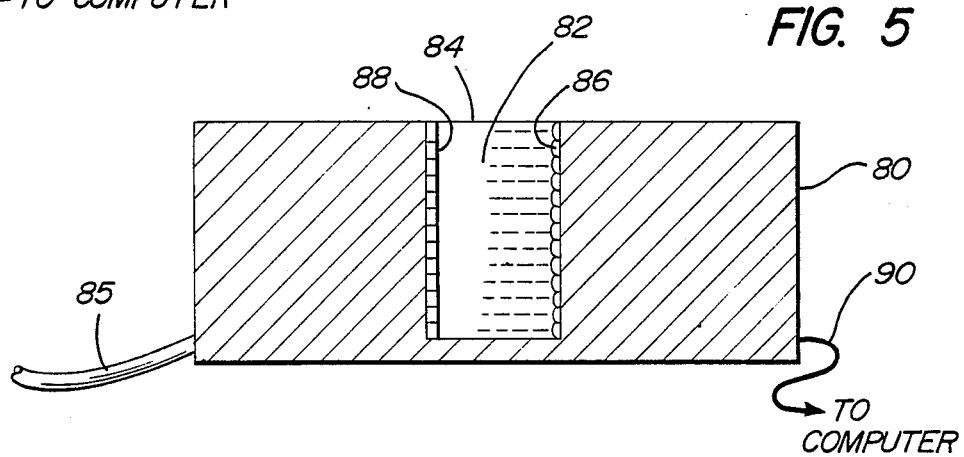
FIG. 5 is a cross-sectional view of an optical sensor of an alternative embodiment of the present invention.

FIG. 5 is a cross-sectional view of an optical sensor unit that may be utilized in an alternative embodiment of the present invention. A housing 80 contains a vertical cavity, generally indicated at 82. The cavity 82 has an opening 84 and is adapted to receive a test tube of conventional construction. The housing 80 is connected to a power source via a power cord 85.

A vertical array of light sources, indicated at 86, is disposed on one side of the cavity 82 and extends from the top of the cavity, near the opening 84, to the bottom. Each light source emits a light beam that extends generally normally to the longitudinal axis of a test tube placed in the cavity 82.

A corresponding vertical array of photosensors, indicated at 88, is disposed on the opposite side of cavity 82 from the vertical array of light sources 86. Each of the photosensors is adapted to receive the light beam transmitted from its corresponding light source and then generate signals proportional to the amplitude of the transmitted beam. The signals outputted by the sensors are provided to the computer 12 via connection line 90.

In this embodiment, the computer 12 analyzes the signals generated by each photosensor after a test tube is placed into the cavity 82 by the robotic arm 10. If the signals do not indicate that the blood specimen is separated into three different layers, then the sample is defective and the robotic arm 10 is controlled to remove the test tube from the sensor 24 and place it in the rejection unit 36. If the centrifuge was successful, the computer 12 determines a level in the test tube to position the sampling needle by locating the lowest photosensor in the array 88 that is generating signals indicative of the blood serum layer.

Figure 4:
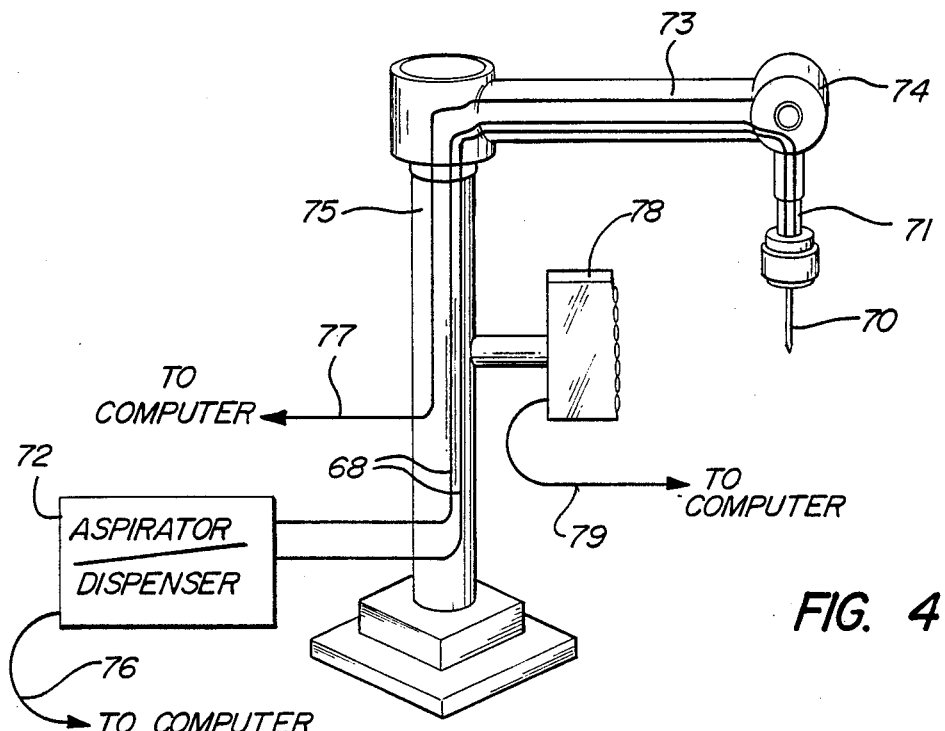
FIG. 4 is a side view of the aspirator/dispenser needle unit of the preferred embodiment of the present invention.

FIG. 4 is a side view of the aspirator/dispenser needle unit of the preferred embodiment of the present invention. A vertically oriented sampling needle 70 is connected to an extendible vertical arm 71 that is supported on an overhead arm 73 by a vertical post 75. The needle 70 is connected to an aspirator/dispenser 72 of conventional construction by a tubing 68. In the preferred embodiment, the needle 70 is positioned directly above the cavity 50 of the optical sensor 24 so that when lowered, the needle 70 may puncture the stopper seal of a test tube resting in the cavity through its center.

The extendible vertical arm 71 is connected to a motor 74 disposed on the overhead arm 73, that controls the vertical position of the needle 70, and may lower the needle into a stopper sealed test tube that is positioned in the optical sensor 24. The overhead arm 73 is also capable of moving laterally to ensure proper positioning of the sampling needle 70 in relation to a test tube below it. The motor 74 and the aspirator/dispenser 72 are connected to the computer 12 via connection lines 77 and 76, respectively. The motor 74 and extendible vertical arm 71 are of conventional construction and controlled by input signals transmitted by the computer 12 through the connection line 77. In an alternative embodiment, the overhead arm 73 may be extendible so that the horizontal position of the needle may also be adjusted.

The preferred embodiment of the present invention also includes a bar code reader 78. The reader 78 is positioned so that the robotic arm 10 may place a bar coded test tube in front of it. The bar code reader 78 is connected to the computer 12 by connection line 79 so that the computer controls when the reader is activated. The computer 12 also receives the information obtained by the activated reader 78 via the connection line 79. In the preferred embodiment, the bar coded test tubes containing whole blood specimens and separator gel are initially loaded into the input rack 16 in a predefined orientation, so that the robotic arm 10 may properly place the processed tubes in front of the bar code reader 78. Alternative embodiments may not include a bar code reader and therefore may not require the test tubes to be initially loaded into rack 16 in predetermined orientations.

The above description is not intended to limit the present invention. It is understood that it is possible to make modifications and variations in light of the above teachings without departing from the present invention.

Having thus described my invention, I claim:

1. The method of inspecting centrifuged test tubes containing whole blood and separator wax, that have been centrifuged to produce separation of the blood into red cells and serum, comprising:
    moving the test tube into an optical sensing unit having at least one light beam extending generally normally to the longitudinal axis of the tube;
    positioning at least one photosensor in said optical sensing unit to receive the light beam transmitted through the tube; and
    analyzing electrical signals generated by the photosensor to: (a) evaluate the success of the separation; and (b) determine the position of the boundary surface between the separator wax and the blood serum.

2. The method of claim 1 wherein said optical sensing unit includes a vertical cavity adapted to receive said test tube, said at least one photosensor being positioned in said cavity to receive a transmitted portion of said at least one light beam for generating electrical signals proportional to a portion of the beam that is occluded.

3. The method of claim 2 wherein the step of analyzing the electrical signals to evaluate the success of separation comprises detecting the number of separate, longitudinally spaced layers in the centrifuged tube by detecting separate time-spaced regions in the electrical signal.

4. The method of claim 2 wherein the step of determining the boundary position between the separator wax and the serum comprises identifying the longitudinal position of the tube relative to the light beam when the electrical signal changes amplitude as a result of transition of the light beam between the separator wax and the serum.

5. The method of claim 2 wherein said at least one light beam is a pulsed infrared sliver of light extending across a diameter of said cavity.

6. The method of claim 1 wherein said optical sensing unit includes a vertical cavity adapted to receive a test tube, said cavity including a vertical array of photosensors disposed on one side of said cavity and a vertical array of corresponding light sources disposed on the opposite side of said cavity, said plurality of light beams extending generally normally to the longitudinal axis of a test tube placed in said optical sensing unit and said matching plurality of photosensors receiving said light beams transmitted through said tube and generating electrical signals proportional to the amplitude of the transmitted beams.

7. The method of claim 6 wherein the step of analyzing the electrical signals to evaluate the success of separation comprises detecting the number of separate, longitudinally spaced layers in the centrifuged tube by detecting differences in the electrical signals generated by said plurality of photosensors.

8. The method of claim 6 wherein the step of determining the boundary position between the separator wax and the serum comprises identifying the position of the tube relative to the location of a photosensor that generates electrical signals indicative of the amplitude of a light beam transmitted through the blood serum.

9. The method of claim 1 wherein said at least one light beam is a pulsed infrared light beam.

10. The method of inspecting stopped test tubes containing whole blood and separator wax that have been centrifuged to produce separation of the blood into red cells and serum and removing the serum from those test tubes that have been successfully separated comprising:
moving the test tube longitudinally relative to a light beam extending generally normally to the longitudinal axis of the tube;
positioning a photosensor to receive the light beam transmitted through the tube;
analyzing electrical signals generated by the photosensor during the motion of the tube relative to the light beam to determine the position of the boundary surface between the separator wax and the blood serum;
inserting a tubular needle having an opening adjacent its extreme end from the exterior of the tube through the tube stopper until the end of the needle is in proximity to the boundary surface between the separator wax and the blood serum as determined by analyzing the electrical signals generated by the photosensor during the motion of the tube relative to the light beam; and
imposing vacuum on the outer end of the tubular needle to draw the serum through the needle and out of the tube.

11. The method of claim 10 wherein said at least one light beam is a pulsed infrared light beam.

12. Apparatus for centrifuging whole blood specimens to separate the serum from the red cells, comprising:
an input station adapted to receive test tubes each containing a whole blood specimen and separator wax;
a centrifuge adapted to rotate the test tubes about an axis inclined with respect to the longitudinal axis of the test tubes so as to separate the whole blood into serum and red cells, separated by a layer of separator wax;
an optical inspection station adapted to receive the test tubes longitudinally relative to at least one light beam extending generally normally to the longitudinal axis and including at least one corresponding photosensor to receive the light beam transmitted through the tube and generate electrical signals proportional to the amplitude of the transmitted beam;
means for receiving the electrical signals generated by the photosensor(s) and analyzing the electrical signals to: (a) evaluate the success of the separation; and (b) determine the position of the boundary surface between the separator wax and the blood serum along the longitudinal axis of the tube;
needle apparatus adapted to be inserted into the tube under control of the electrical signals which determine the position of the boundary surface of the separator wax and the blood's serum so that the free end of the needle is positioned immediately adjacent said boundary surface;
suction means for drawing the serum out of the test tube through the needle;
means for dispensing serum that was drawn in said needle by said suction means, through and out of said needle;
a pair of output stations for receipt of successfully separate test tubes and unsuccessfully separated test tubes; and
a robotic arm adapted to remove the test tubes, one at a time, from said input station and move them to the centrifuge, remove the centrifuged test tubes and place them in the optical inspection station, and remove the optically inspected test tubes and place them into either said first or second output station under control of the means for evaluating the electrical signals to determine the success of the separation operation.

13. The apparatus of claim 12 further including a feeder station adapted to receive and dispense empty containers, said containers being adapted to receive and retain blood serum samples that are dispensed from said needle apparatus.

14. The apparatus of claim 13 wherein said robotic arm is also adapted to, upon said means for analyzing said electrical signals generated by the photosensor(s) determining that the separation operation was a success, remove an empty container from said feeder station and move it to a position underneath said needle apparatus.

15. The apparatus of claim 14 including dispenser means for dispensing the serum out of said needle into said container held by said robotic arm, and wherein said robotic arm is adapted to move said container holding the blood serum together with said test tube from which the serum was withdrawn to said output station for successfully separated test tubes.

16. The apparatus of claim 12 further including identifier means connected to said means for receiving the photosensor electrical signals and operative to identify test tubes.

17. The method of claim 12 wherein said at least one light beam is a pulsed infrared light beam.

* * * * *